(12) United States Patent
Deshpande et al.

(10) Patent No.: US 7,223,863 B2
(45) Date of Patent: May 29, 2007

(54) PROCESS FOR PREPARING TADALAFIL AND ITS INTERMEDIATE

(75) Inventors: Pandurang Balwant Deshpande, Vadodara (IN); Bharat Becharbhai Boda, Vadodara (IN); Sachin Surendra Surti, Vadodara (IN); Pranay Pravinchandra Shah, Vadodara (IN)

(73) Assignee: Alembic Limited, Gujarat (IN)

( * ) Notice: Subject to any disclaimer, the term of this patent is extended or adjusted under 35 U.S.C. 154(b) by 0 days.

(21) Appl. No.: 11/492,246

(22) Filed: Jul. 25, 2006

(65) Prior Publication Data

US 2006/0258865 A1    Nov. 16, 2006

(30) Foreign Application Priority Data

Oct. 31, 2005    (IN) .................... 1374/MUM/2005

(51) Int. Cl.
*C07D 405/14* (2006.01)
*C07D 405/04* (2006.01)
(52) U.S. Cl. ........................... 544/343; 546/85
(58) Field of Classification Search ............... 544/343; 546/85
See application file for complete search history.

(56) References Cited

OTHER PUBLICATIONS

Zhang, Y. et al.: Improved synthesis of Tadalafil. Organic prep. and proceed. Intern., vol. 37, pp. 99-102, 2005.*

\* cited by examiner

*Primary Examiner*—Charanjit S. Aulakh

(74) *Attorney, Agent, or Firm*—Hamre, Schumann, Mueller & Larson, PC

(57) ABSTRACT

The present invention relates an improved process for the preparation of tetrahydro-β-carboline derivative of formula (V) which is useful as an intermediate for the preparation of Tadalafil of formula (I). Moreover, the present invention relates to the process for the preparation of Tadalafil of formula (I)

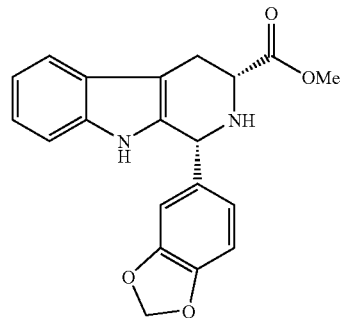

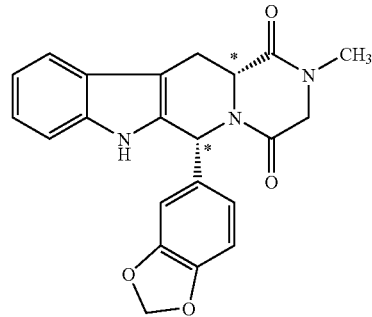

11 Claims, No Drawings

PROCESS FOR PREPARING TADALAFIL AND ITS INTERMEDIATE

FIELD OF THE INVENTION

The present invention relates an improved process for the preparation of tetrahydro-β-carboline derivative of formula (V) which is useful as an intermediate for the preparation of Tadalafil of formula (I). Moreover, the present invention relates to the process for the preparation of Tadalafil of formula (I)

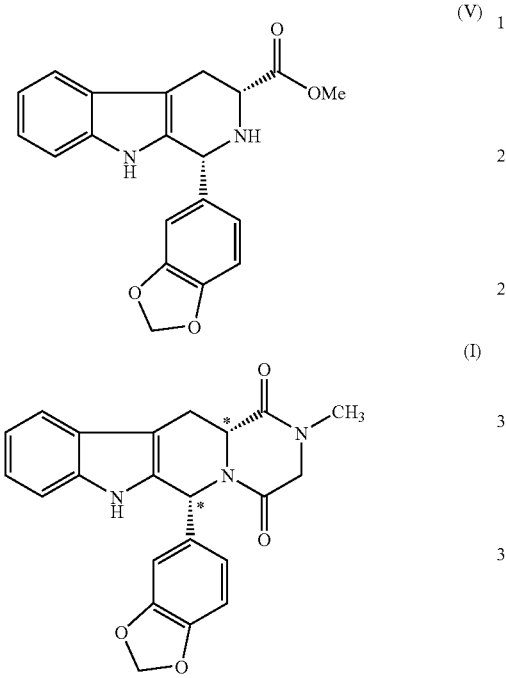

BACKGROUND OF THE INVENTION

The chemical name of Tadalafil is (6R, 12aR)-2, 3, 6, 7, 12, 12a-hexahydro-2-methyl 6-(3,4-methylenedioxyphenyl)-pyrazino[2', 1': 6,1]pyrido [3,4-b]indole-1, 4-dione and molecular formula is $C_{22}H_{19}N_3O_4$ and molecular weight is 389.41. The current pharmaceutical product contaning this drug is being sold by Icos-Lilly using tradename CIALIS, in the form of tablets.

Tadalafil of formula (I) is a tetra cyclic derivative, potent and selective inhibitor of cyclic guanosine 3,5-monophosphate-(cGMP)-specific phosphodiesterase type 5(PDE5) having utility in a variety of therapeutic area where such inhibition is thought to be beneficial. Therefore, it has utility in the treatment of various disorders, including stable, unstable and variant (Prinzmetal) angina, hypertension pulmonary hypertension, congestive heart failure, renal failure, arteiosclerosis, conditions of reduced blood vessel potency (post-PTCA) etc. Tadalafil is potent drug useful for treatment of erectile dysfunction.

U.S. Pat. No. 5,859,006 describes a process for the preparation of Tadalafil and its intermediate of formula (V) which involves reacting D-Tryptophan methyl ester of formula

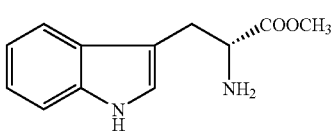

With a piperonal of formula

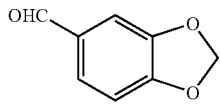

in the presence of dichloromethane and trifluoroacetic acid which provides cis and trans isomers of compound of formula (V). The isomers are separated by chromatography. The cis isomer is then reacted with chloroacetyl chloride and methylamine to give Tadalafil of formula (I). The product of the reaction was purified by chromatography.

The above process has the certain disadvantages such as:
(a) The above process is time consuming and requiring 4–5 days at 0–5° C. for the completion of reaction.
(b) Overall yield obtained is low, with 37–42% cis isomer of (V), which is desired, and 27–47% trans isomer of (V) (undesired).
(c) It uses highly corrosive and toxic material Trifluoroacetic acid.
(d) All these processes require either fractional crystallization or column chromatography of the reaction mixture in order to separate the isomers before epimerization to form pure cis isomer of (V).
(e) The process requires 24–72 hours for epimerization in a volatile solvent like dichloromethane.

WO2004/011463 discloses process of preparation of Tadalafil via modified pictate-spengler reaction in which D-Tryptophan methyl ester hydrochloride and piperonal is condensed in anhydrous IPA to provide hydrochloride of compound of formula (V). The product further is reacted with chloroacetyl chloride and then with methyl amine to give Tadalafil of formula (I).

However this process requires anhydrous IPA specifically 0.1% or less water which is practically difficult thing.

WO2005/068464 discloses process of preparation in which D-Tryptophan methyl ester and piperonal is condensed in the presence of TFA, solvent and molecular sieves to give mixture of compound of formula (V) as cis and trans isomers which is treated with aq HCl to form hydrochloride salt of cis isomer which inturn is reacted with chloroacetyl chloride and then methylamine to give Tadalafil of formula (I).

However, in this process highly toxic and corrosive reagent trifloroacetic acid is used which should be avoided normally for regulatory compliance purpose.

In summary, the prior art relating to the process for the preparation of Tadalafil suffers with several drawbacks such as:
(a) The processes given in are time consuming and requiring 4–5days at 0–5° C. for the completion of reaction.
(b) Overall yield obtained is low, with 37–42% cis isomer of (V), which is desired, and 27–47% trans isomer of (V) (undesired).
(c) Highly corrosive and toxic material Trifluoroacetic acid is used in several patents.

(d) The processes require either fractional crystallization or column chromatography of the reaction mixture in order to separate the isomers before epimerization to form pure cis isomer of (V). The process also requires 24–72 hours for epimerization in a volatile solvent like dichloromethane.
(e) The process requires critical moisture check of the solvent like IPA in some patent.

The present inventors have directed their research work toward developing a process which solves above mentioned problems that is associated with the existing process.

Hence, there is need to overcome problems by developing an improved process, particularly processes that directly synthesize desired stereoisomer of the compound.

OBJECT OF THE INVENTION

It is therefore an object of the present invention to provide an improved process for the preparation of Tadalafil of formula (I).

Another object of the present invention is to provide a process for the preparation of compound of formula (V) via in-situ conversion of the undesired trans isomer of (V) into a cis isomer of (V) with improved yield and quality.

Another object of the present invention is to provide a process in which the cis isomer of compound of formula (V) is obtained as major product.

A further object of the present invention is to provide a procedure which eliminates the use of volatile solvent as well as such solvent condition in which a regular moisture content (being below 0.1%) check is required.

Yet another object of the present invention is to provide simple procedure which eliminates the use of highly corrosive and hazardous chemicals such as TFA.

Still another object of the present invention is to provide a process which eliminate the use of chromatographic purification at various stages and can be useful at commercial scale.

SUMMARY OF THE INVENTION

Accordingly, present invention provides an improved process of preparation of Tadalafil comprising steps of:
(i) reacting D-Tryptophan methyl ester hydrochloride of formula (III) with piperonal of formula (IV) in the presence of dehydrating agent and in the presence of high boiling solvent to obtain compound of formula (V) as mixture of cis and trans isomer which is reacted further without isolating and separating isomers with an aqueous HCl to provide hydrochloride salt of cis isomer of compound of formula (V) as major isomer which optionally is crystallized by precipitation methods.

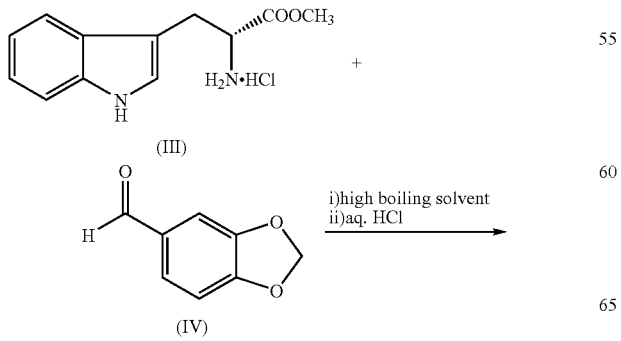

(ii) reacting the compound of formula (V) obtained hereinabove step with chloroacetyl chloride in the presence of base and an organic solvent to get intermediate of formula (VI) which is further reacted with aqueous methylamine solution to obtain crude which is purified by recrystallization to get Tadalafil of formula (I).

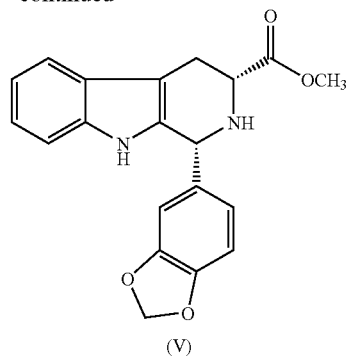

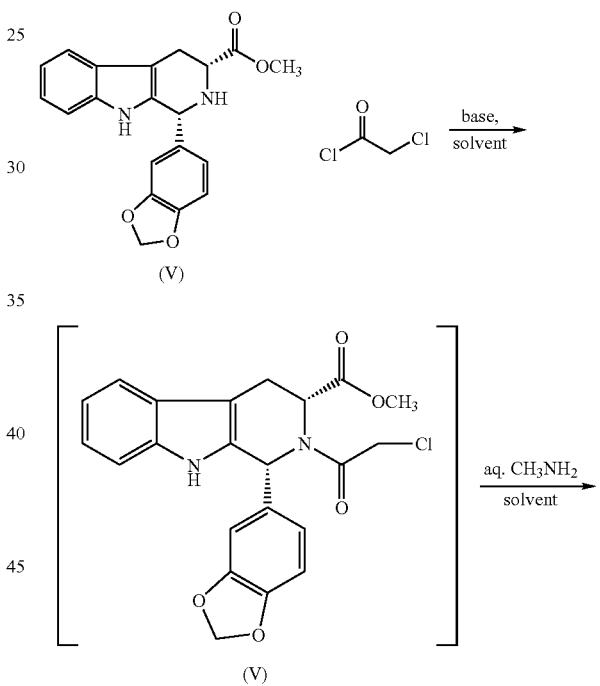

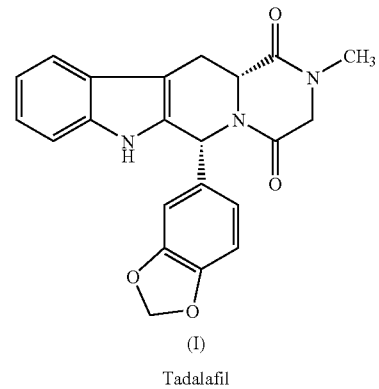

(I)
Tadalafil

DETAILED DESCRIPTION OF THE INVENTION

The step (i) is of the process as mentioned above is carried out at a temperature in a range of from about 65° C. to about 70° C. in the presence dehydrating agent and high boiling solvent.

The example of high boiling solvent as mentioned in step (i) herein above includes but not limited to N,N-Dimethyl acetamide, Dimethyl sulfoxide, N,N-dimethyl formamide, N-methyl pyrrolidine and the like or the mixture thereof. The preferred solvent is N,N-Dimethyl acetamide.

The dehydrating agent as mentioned in step (i) herein above is selected from the group comprising alkali or alkaline earth metal sulphates; alkaline earth metal chlorides or molecular sieves. The example of dehydrating agent as mentioned in step (i) herein above includes but not limited to $Na_2SO_4$, $K_2SO_4$, $MgSO_4$, $CaSO_4$, $CaCl_2$, molecular sieve and the like or the mixture thereof. The preferred dehydrating agent is sodium sulphate.

After completion of the reaction the reaction mixture is basified with base such as alkali or alkaline earth metal bicarbonate, carbonate or hydroxide or mixture thereof either as solid or as aqueous solution. The base is selected from $NaHCO_3$, $KHCO_3$, $LiHCO_3$, $CaCO_3$, $Na_2CO_3$, $K_2CO_3$, NaOH, KOH, LiOH. The preferred base is $NaHCO_3$.

The mass is extracted with a suitable organic solvent like chlorinated hydrocarbon such as MDC, EDC, chloroform; ester like ethyl acetate, methyl ethyl ketone; ether such as diethyl ether; aromatic hydrocarbons such as toluene, benzene, xylene and the like. The preferred extracting solvent is dichloromethane.

The organic layer is then treated with aqueous hydrochloric acid whereby distilling out organic solvent below 60° C. and heating the reaction mass at the temperature from about 40° C. to about 70° C. preferably at from 55° C. to 60° C. for the period of time sufficient for the conversion to take place. Generally it takes 6–10 hours to complete.

After completion of the reaction the mass is cooled to ambient temperature (from about 25° C. to about 35° C.). The resulting hydrochloride salt is recovered by methods such as filtration, decantation or centrifugation.

The hydrochloride salt is treated with base such as alkali or alkaline earth metal bicarbonate, carbonate or hydroxide as solution to make the free compound of formula (V). The example of base includes but not limited to $NaHCO_3$, $KHCO_3$, $Na_2CO_3$, $K_2CO_3$, $CaCO_3$, NaOH, KOH and the like or the mixture thereof. The example of preferred base is $NaHCO_3$. The product is isolated by extracting the solution in a suitable organic solvent such as Ethyl acetate, MDC, EDC and the like preferably from dichloromethane. The product is optionally charcoalized and the solvent is evaporated under reduced pressure to give the crude compound of formula (V).

The crude compound is dissolved in a non-polar solvent and product is precipitated by addition of antisolvent.

The term "precipitation" referes hereinabove means dissolving solid material in a solvent in which it dissolves and precipitation by adding a solvent in which compound is partially soluble or less soluble.

The example of non-polar solvent includes but not limited to toluene, ethyl acetate, dichloromethane and the like or the mixture thereof.

The example of antisolvent includes but not limited to cyclohexane, hexane, pantane, cyclopentane, heptane and the like or mix thereof.

In the preferred embodiment toluene is used as solvent and cyclohexane is used as antisolvent. The product is isolated by conventional methods such as filtration, decantation or centrifugation and the like. The product is dried at temperature range from about 55° C. to 60° C.

The step (ii), preparation of compound of formula (VI) is done by the conventional method well known in the art. Compound of formula (V) obtained hereinabove is reacted with chloroacetyl chloride in the presence of base and an organic solvent at a temperature from about 0° C. to about 5° C.

The example of base includes but not limited to alkali or alkaline earth metal bicarbonate, carbonate or mix thereof such as $NaHCO_3$, $KHCO_3$, $LiHCO_3$, $Na_2CO_3$, $K_2CO_3$, $Li_2CO_3$, $CaCO_3$.

After completion of the reaction, the mass is quenched in water and the organic layer is separated. The organic phase is washed with basic solution. The removal of the solvent from organic phase provides residue of formula (VI).

The residue of formula (VI) is dissolved in suitable alcohol solvent to which an aqueous methylamine solution is added and stirred at ambient temperature. The mass is heated to a temperature from about 55° C. to about 60° C. for sufficient period of time for the reaction to take place.

After completion of reaction, the mass is cooled to ambient temperature and then isolated by methods such as filtration, decantation or centrifugation. The material is dried at a temperature ranging from about 60° C. to about 65° C. to get the Tadalafil of formula (I) as crude.

The crude is dissolved in suitable organic solvent or solvent mixture and optionally charcoalized. The removal of solvent from the filtrate gives residue which is crystallized from isopropanol.

The starting material D-Tryptophan methyl ester hydrochloride is prepared as per the method known in the art.

In another embodiment, the process of preparation of Tadalafil comprises the steps of:

(i) reacting D-Tryptophan of formula (II) with thionyl chloride in methanol at reflux temperature for 2–4 hours to get D-Tryptophan the crude product which is crystallized from the mixture of toluene and methanol to give D-Tryptophan methyl ester hydrochloride of formula (III).

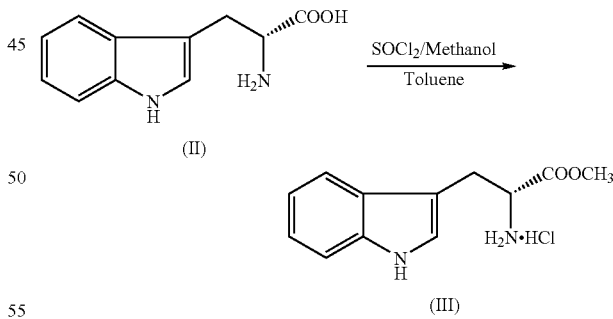

(ii) reacting D-Tryptophan methyl ester hydrochloride of formula (III) with piperonal of formula (IV) in the presence of dehydrating agent and in the presence of high boiling solvent to obtain compound of formula (V) as mixture of cis and trans isomer which is reacted further without isolating and separating isomers with an aqueous HCl to provide hydrochloride salt of cis isomer of compound of formula (V) as major isomer which inturn is made free from the salt and purified by crystallization as solvent-antisolvent treatment.

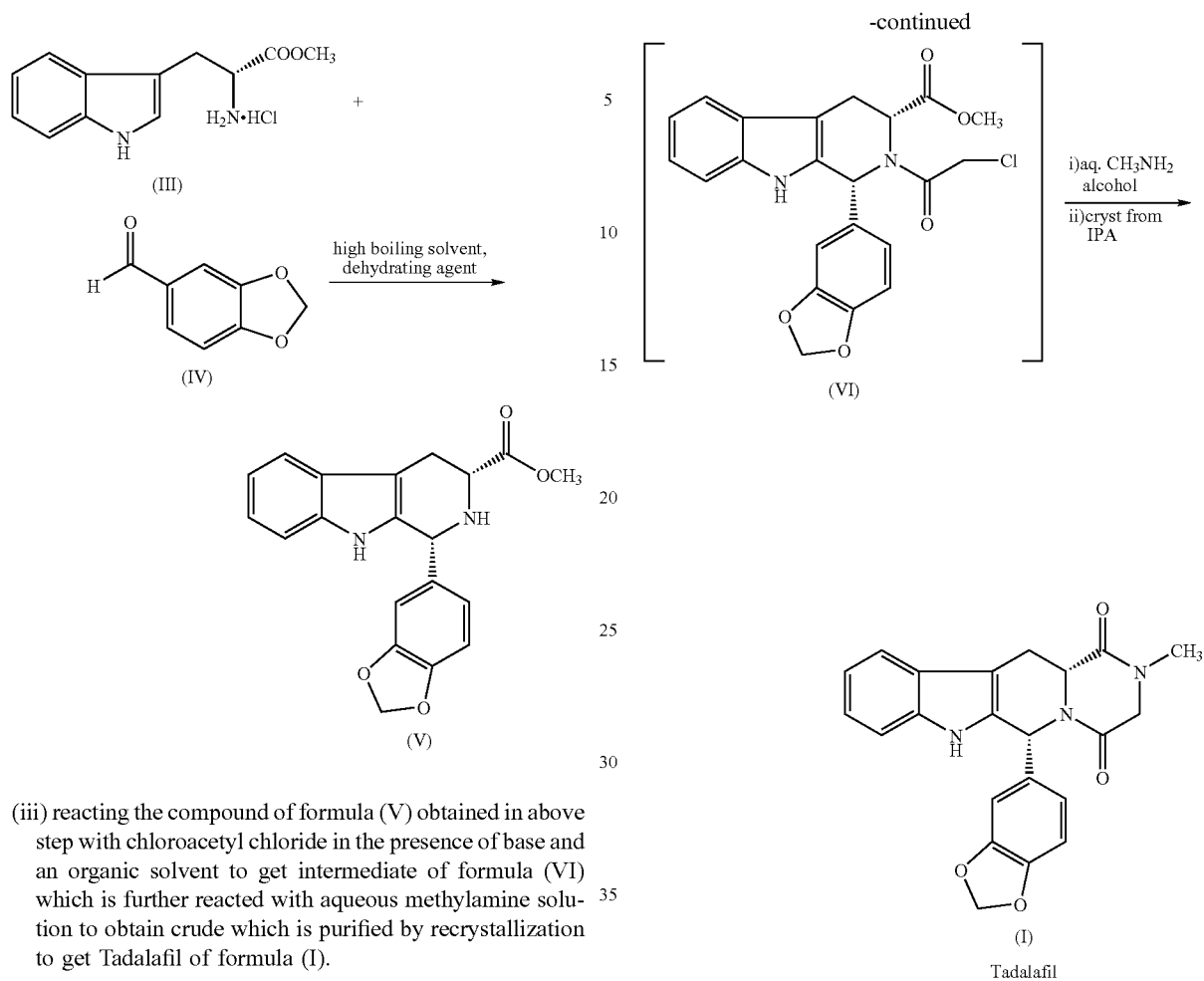

(iii) reacting the compound of formula (V) obtained in above step with chloroacetyl chloride in the presence of base and an organic solvent to get intermediate of formula (VI) which is further reacted with aqueous methylamine solution to obtain crude which is purified by recrystallization to get Tadalafil of formula (I).

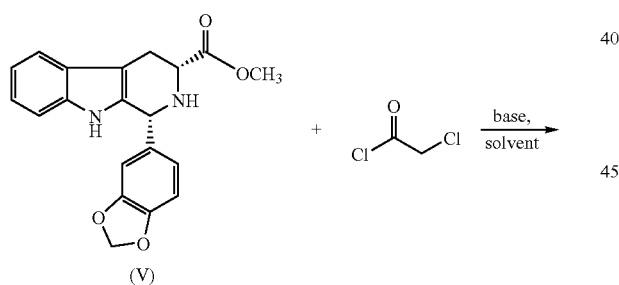

The complete representation of the process for the preparation of Tadalafil as provided by the present invention is depicted by the following schematic diagram:

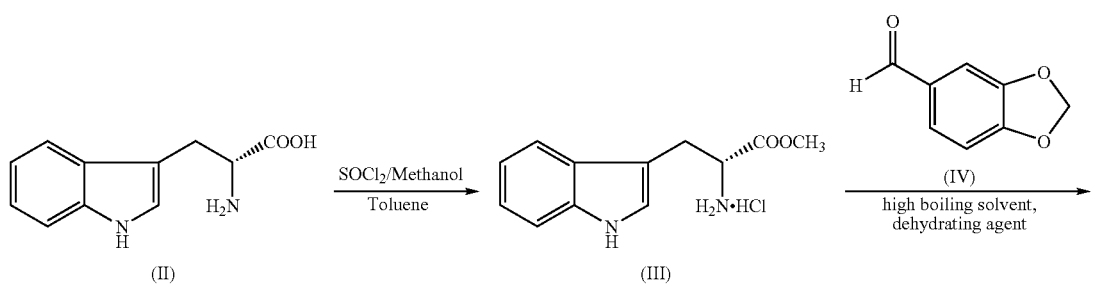

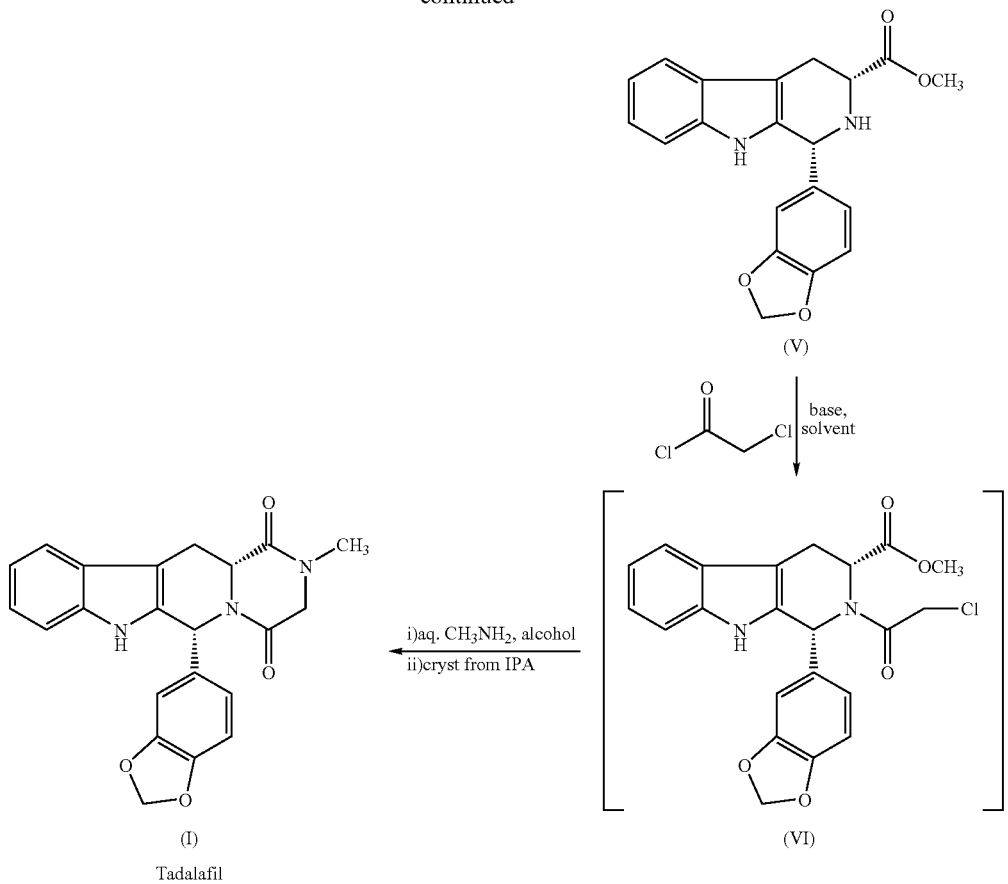

The process of the present invention has following advantage:
(a) It avoids corrosive and toxic reagent such as trifluoroacetic acid.
(b) The duration of reaction period is relatively shorter.
(c) The overall yield for getting cis isomer is high.
(d) The process is simple easy to handle and provides better yield and improved quality.
(e) It provides relatively pure Tadalafil of formula without repeated crystallization or column chromatographic purification
(f) The solvent used for epimerization is relatively non-volatile and it need not require critical moisture content check as the presence of dehydrating agent is sufficient to overcome the problem.

The following examples illustrate the invention further. It should be understood, however, that the invention is not confined to the specific limitations set forth in the individual examples but rather to the scope of the appended claims.

EXAMPLES

Example-1

Preparation of (1R, 3R)-Methyl-1,2,3,4-tetrahydro-1 (3,4-methylenedioxyphenyl)-9H-pyrido[3,4-b]indole-3-carboxylate To a solution of D-Tryptophan methyl ester hydrochloride (100 g) in N,N-Dimethyl acetamide (500 ml), added Piperonal (65 g) and sodium sulphate (56 g) and heated the reaction mass to 65–70° C. for 30–35 hours for completion of reaction. Reaction mass is then diluted with water, basified with sodium bicarbonate solution and extracted twice with dichloromethane (2×750 ml). The organic layer is then treated with aqueous hydrochloric acid (1000 ml). Dichloromethane is evaporated and the reaction mass is stirred for 6–10 hours at 55–60° C. Cooled the reaction mass to an ambient temperature and filtered the crude title compound in hydrochloride salt form. Then wet crude mass is charged in sodium bicarbonate solution and extracted twice with dichloromethane (2×750 ml). Dichloromethane layer is distilled out and the residual material is dissolved in Toluene and crystallized by addition of anti solvent like cyclohexane to get title compound (89.0 g).

Mp: 154–155° C.

$[\alpha]_D^{20°}$=+24.4° (c=1.03, CHCl$_3$)

Example-2

Preparation of Tadalafli

To a cooled suspension of (1R,3R)-Methyl-1,2,3,4-tetrahydro-1-(3,4-methylenedioxy phenyl)-9H-pyrido[3,4-b]indole-3-carboxylate (100 g) and Sodium bicarbonate (30 g) in Dichloromethane (2000 ml) at 0° C., Chloroacetylchloride (57 ml) was added maintaining temperature between 0° and 5° C. The reaction mixture was stirred at 0–5° C. for 1–3 hrs. The progress of the reaction was monitored on TLC. After completion of reaction, the reaction mixture was diluted with dichloromethane (2000 ml), washed with Sodium bicarbonate and then by water. Dichloromethane was evaporated from organic phase and n-Propanol (1500 ml) was charged to the residue. Aqueous Methylamine solution (40% in water) (111 ml) was added to the above reaction mixture and heated to 55–60° C. for 4–10 hours. The progress of the reaction was monitored on TLC. After completion of reaction, the mixture was cooled at 25–35° C. The solid was filtered and washed the wet cake with methanol (2×50 ml). The solid was recrystallized from 2-propanol to give title compound (85 g).

Mp: 302–303° C.
$[\alpha]_D^{20°} = +71.0°$ (c=1.00, CHCl$_3$)

Example-3

Preparation of (1R, 3R)-Methyl-1,2,3,4-tetrahydro-1 (3,4-methylenedioxyphenyl)-9H-pyrido[3,4-b]indole-3-carboxylate To a solution of D-Tryptophan methyl ester hydrochloride (100 g) in N,N-Dimethyl acetamide (500 ml), added Piperonal (65 g) and magnesium sulfate (47.32 g) and heated the reaction mass to 65–70° C. for 30–35 hours for completion of reaction. Reaction mass is then diluted with water, basified with sodium bicarbonate solution and extracted twice with dichloromethane (2×750 ml). The organic layer is then treated with aqueous hydrochloric acid (1000 ml). Dichloromethane is evaporated and the reaction mass is stirred for 6–10 hours at 55–60° C. Cooled the reaction mass to an ambient temperature and filtered the crude title compound in hydrochloride salt form. Then wet crude mass is charged in sodium bicarbonate solution and extracted twice with dichloromethane (2×750 ml). Dichloromethane layer is distilled out and the residual material is dissolved in Toluene and crystallized by addition of anti solvent like cyclohexane to get title compound (88.0 g).

mp: 153–155° C.
$[\alpha]_D^{20°} = +24.4°$ (c=1.03, CHCl$_3$)

Example-4

Preparation of (1R, 3R)-Methyl-1,2,3,4-tetrahydro-1 (3,4-methylenedioxyphenyl)-9H-pyrido[3,4-b]indole-3-carboxylate To a solution of D-Tryptophan methyl ester hydrochloride (100 g) in N,N-Dimethyl acetamide (500 ml), added Piperonal (65 g) and heated the reaction mass to 65–70° C. for 30–35 hours for completion of reaction. Reaction mass is then diluted with water, basified with sodium bicarbonate solution and extracted twice with dichloromethane (2×750 ml). The organic layer is then treated with aqueous hydrochloric acid (1000 ml). Dichloromethane is evaporated and the reaction mass is stirred for 6–10 hours at 55–60° C. Cooled the reaction mass to an ambient temperature and filtered the crude title compound in hydrochloride salt form. Then wet crude mass is charged in sodium bicarbonate solution and extracted twice with dichloromethane (2×750 ml). Dichloromethane layer is distilled out and the residual material is dissolved in Toluene and crystallized by addition of anti solvent like cyclohexane to get title compound (88.0 g).

mp: 154–155° C.
$[\alpha]_D^{20°} = +24.4°$ (c=1.03, CHCl$_3$).

The invention claimed is:

1. A process for the preparation of Tadalafil comprising a step of reacting an acid addition salt of D-Tryptophan methyl ester of formula (IIIa)

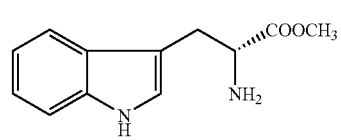

with piperonal of formula (IV)

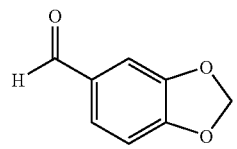

in the presence of high boiling solvent wherein high boiling solvent is selected from N,N-Dimethyl acetamide, Dimethyl sulfoxide, N,N-dimethyl formamide, N-methyl pyrrolidine or mixture thereof and in the presence of dehydrating agent to obtain compound of formula (V)

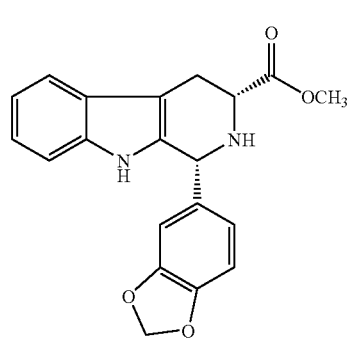

2. A process for the preparation of Tadalafil comprising a step of reacting D-Tryptophan methyl ester hydrochloride of formula (III)

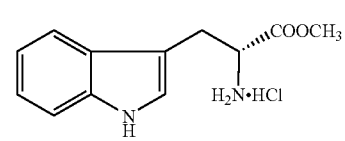

with piperonal of formula (IV)

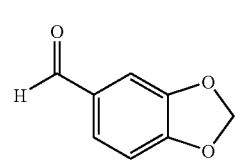

in the presence of dehydrating agent and high boiling solvent wherein high boiling solvent is selected from N,N-Dimethyl acetamide, Dimethyl sulfoxide, N,N-dimethyl formamide, N-methyl pyrrolidine or mixture thereof to obtain compound of formula (V)

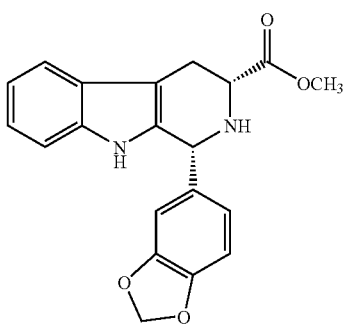

as mixture of cis and trans isomer which is reacted further without isolating and separating isomers with an aqueous HCl to provide hydrochloride salt of cis isomer of compound of formula (V) as major isomer.

3. A process of preparation of Tadalafil comprising steps of
(i) reacting D-Tryptophan methyl ester hydrochloride of formula (III)

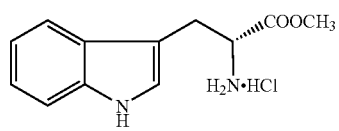

with piperonal of formula (IV)

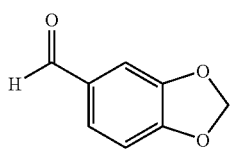

in the presence of dehydrating agent and high boiling solvent wherein high boiling solvent is selected from N,N-Dimethyl acetamide, Dimethyl sulfoxide, N,N-dimethyl formamide, N-methyl pyrrolidine or mixture thereof to obtain compound of formula (V)

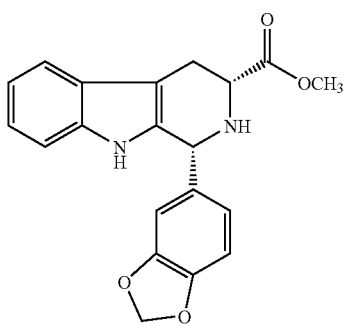

as mixture of cis and trans isomer which is reacted further without isolating and separating isomers with an aqueous HCl to provide hydrochloride salt of cis isomer of compound of formula (V) as major isomer (ii) reacting the compound of formula (V) obtained hereinabove step with chloroacetyl chloride in the presence of base and an organic solvent to get intermediate of formula (VI)

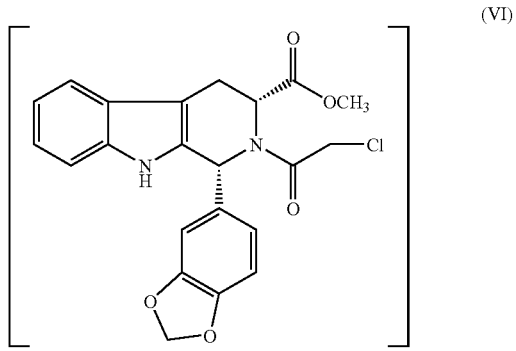

which is further reacted with aqueous methylamine solution to obtain Tadalafil of formula (I)

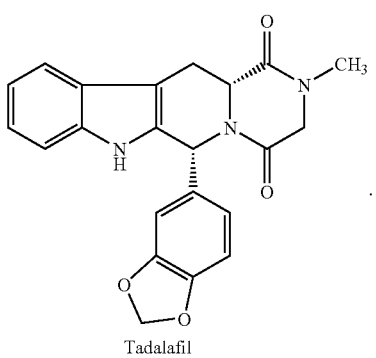

Tadalafil

4. A process as claimed in claim 1, wherein dehydrating agent is selected from $Na_2SO_4$, $K_2S_{O4}$, $MgSO_4$, $CaSO_4$, $CaCl_2$, molecular sieve or mixture thereof.

5. A process as claimed in claim 4, wherein dehydrating agent is $Na_2SO_4$.

6. A process as claimed in claim 1, wherein high boiling solvent is N,N-Dimethyl acetamide.

7. A process as claimed in claim 3, wherein base is selected from a group comprising alkali or alkaline earth metal bicarbonate, carbonate or mix thereof.

8. A process as claimed in claim 7, wherein base is selected from $NaHCO_3$, $KHCO_3$, $LiHCO_3$, $Na_2CO_3$, $K_2CO_3$, $Li_2CO_3$, $CaCO_3$ or mixture thereof.

9. A process as claimed in claim 3, wherein organic solvent in step (ii) is dichloromethane.

10. A process as claimed in claim 2, wherein the dehydrating agent is selected from $Na_2SO_4$, $K_2SO_4$, $MgSO_4$, $CaSO_4$, $CaCl_2$, molecular sieve or mixture thereof.

11. A process as claimed in claim 3, wherein the dehydrating agent is selected from $Na_2SO_4$, $K_2SO_4$, $MgSO_4$, $CaSO_4$, $CaCl_2$, molecular sieve or mixture thereof.

* * * * *